United States Patent
Wu et al.

(10) Patent No.: US 10,150,739 B2
(45) Date of Patent: Dec. 11, 2018

(54) CRYSTALLINE FORM OF ANDROGEN RECEPTOR INHIBITOR AND PREPARATION METHOD THEREOF

(71) Applicant: Jiangsu Hengrui Medicine Co., Ltd., Lianyungang, Jiangsu (CN)

(72) Inventors: Guaili Wu, Jiangsu (CN); Changshan Guo, Jiangsu (CN); Liang Zhong, Jiangsu (CN); Yun Lu, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 15/757,652

(22) PCT Filed: Aug. 23, 2016

(86) PCT No.: PCT/CN2016/096381
§ 371 (c)(1),
(2) Date: Mar. 5, 2018

(87) PCT Pub. No.: WO2017/041622
PCT Pub. Date: Mar. 16, 2017

(65) Prior Publication Data
US 2018/0244628 A1 Aug. 30, 2018

(30) Foreign Application Priority Data

Sep. 10, 2015 (CN) .......................... 2015 1 0574141
Feb. 2, 2016 (CN) .......................... 2016 1 0073458

(51) Int. Cl.
*C07D 233/86* (2006.01)
*A61K 31/4166* (2006.01)
*A61P 35/00* (2006.01)

(52) U.S. Cl.
CPC ........ *C07D 233/86* (2013.01); *A61K 31/4166* (2013.01); *A61P 35/00* (2018.01); *C07B 2200/13* (2013.01)

(58) Field of Classification Search
CPC .................................................. C07D 233/86
See application file for complete search history.

(56) References Cited

U.S. PATENT DOCUMENTS

| 2011/0306615 A1 | 12/2011 | Tachibana |
| 2012/0184580 A1 | 7/2012 | Chakravarty |
| 2015/0225381 A1 | 8/2015 | Lu et al. |

FOREIGN PATENT DOCUMENTS

| CN | 101048381 A | 10/2007 |
| CN | 101222922 A | 7/2008 |
| WO | 2006124118 A1 | 11/2006 |
| WO | 2010118354 A1 | 10/2010 |
| WO | 2014036897 A1 | 3/2014 |
| WO | 2017041622 A1 | 3/2017 |

OTHER PUBLICATIONS

International Search Report dated Nov. 18, 2016 for International Application No. PCT/CN2016/096381. (6 pages).

*Primary Examiner* — Paul V Ward
(74) *Attorney, Agent, or Firm* — Panitch Schwarze Belisario & Nadel LLP (57) ABSTRACT

A crystalline form of an androgen receptor inhibitor and its preparation method are provided. In particular, provided are crystal form I of (S)-4-(3-(4-(2,3-dihydroxypropoxy)phenyl)-4,4-dimethyl-5-carbonyl-2-thioimidazolin-2-yl)-2-(trifluoromethyl)benzonitrile (a compound of formula (I)) and its preparation method. The method includes (a) adding any crystal form or amorphous form of the compound of formula (I) to an organic solvent to obtain a solution and heating the solution until it is clear, followed by cooling the solution to precipitate a crystal; and (b) filtering, washing, and drying the crystal. The obtained crystal form I of the compound of formula (I) has good chemical stability and crystal form stability, and the crystallization solvent used has low toxicity and residue, and is thus better for use in clinical treatment.

16 Claims, 6 Drawing Sheets

CRYSTALLINE FORM OF ANDROGEN RECEPTOR INHIBITOR AND PREPARATION METHOD THEREOF

CROSS-REFERENCE TO RELATED APPLICATION

This application is a Section 371 of International Application No. PCT/CN2016/096381, filed Aug. 23, 2016, which was published in the Chinese language on Mar. 16, 2017, under International Publication No. WO 2017/041622 A1, which claims priority under 35 U.S.C. § 119(b) to Chinese Application No. 201510574141.9, filed Sep. 10, 2015, and Chinese Application No. 201610073458.9, filed Feb. 2, 2016, the disclosures of which are incorporated herein by reference in their entirety.

FIELD OF THE INVENTION

The present invention relates to crystal form I of (S)-4-(3-(4-(2,3-dihydroxypropoxy)phenyl)-4,4-dimethyl-5-carbonyl-2-thioimidazolin-1-yl)-2-(trifluoromethyl)benzonitrile and a preparation method thereof.

BACKGROUND OF THE INVENTION

Prostate cancer (PCa) is a malignant tumor that occurs in the prostate tissue of males, and is the result of abnormal growth of prostate acinar cells. The differentiation and growth of normal prostate epithelial cells as well as the development of prostate cancer all depend on androgen, which is mainly (about 80-90%) synthesized in the testes. Synthetic androgen binds to the androgen receptor (AR) after entering the cells, causing dissociation of heat shock protein (HSP) from AR, then the AR enters the nucleus and activates multiple downstream genes, including prostate-specific antigen (PSA). Early prostate cancer is sensitive to androgen, orchiectomy (castration) can thus significantly inhibit the development of prostate cancer. Although castration surgery is effective for a certain period of time, many patients undergo the transformation of androgen-dependent to androgen-independent during a period of time after castration. The prostate cancer of these patients develops into androgen independent prostate cancer (AIPC), and anti-androgen therapy is no longer effective to them. The occurrence of AIPC still has an important relationship with activation of the AR signaling pathway in PCa cells.

First-generation drugs, which aim at inhibiting AR activity, include Bicalutamide (or Casodex) and Flutamide. Second-generation AR antagonist drugs for AIPC therapy include MDV3100 and ARN-509. MDV3100 is the first second-generation non-steroidal AR antagonist drug in the world, and was approved by the U.S. Food and Drug Administration (FDA) at the end of August 2012. The affinity of MDV-3100 to AR is 5-8 times higher than that of bicalutamide. MDV-3100 can inhibit the growth of AIPC in mouse and human by inhibiting AR activity, and has no effect of promoting tumor cell growth.

MDV-3100

ARN-509

International Patent Application Publication WO2014036897A1 discloses novel AR antagonists, comprising a compound of formula (I). The activity in vitro of this compound is slightly better than that of MDV-3100, and the hERG inhibition rate is further improved (IC50:24.83 µM). The inhibition half-lives of this compound toward five major subtypes of CYP450 are all greater than 50 µM. The in vivo exposure of this compound in rats is comparable to that of MDV-3100, and the in vivo exposure of this compound in dogs is more than six times that of MDV-3100 at the same dose and in the same solvent. The compound of formula (I) has only one chiral center. The chiral starting material is easy to obtain, and the synthesis difficulty is greatly reduced. In addition, the compound of formula (I) has no AR agonist activity at 3 µM and 10 µM, and the ratio of drug concentration in brain tissue to drug concentration in plasma in mice is much lower than that of MDV-3100 compound, and the possibility of epileptic side effects is smaller. Therefore, the compound of formula (I) has broad clinical prospects.

(I)

However, International Patent Application Publication WO2014036897A1 does not further investigate the crystal form of this compound. It is known to those skilled in the art that the crystal structure of a pharmaceutically active ingredient often affects the chemical stability of the drug. Different crystallization conditions and storage conditions can lead to changes in the crystal structure of the compound, and sometimes accompany production of other crystal forms. In general, an amorphous drug product does not have a regular crystal structure, and often has other defects, such as poor product stability, smaller particle size, difficult filtration, easy agglomeration, and poor liquidity. Therefore, it is necessary to improve the various properties of the above compound. There is a need to find a new crystal form with high purity and good chemical stability.

SUMMARY OF THE INVENTION

Figure 1:
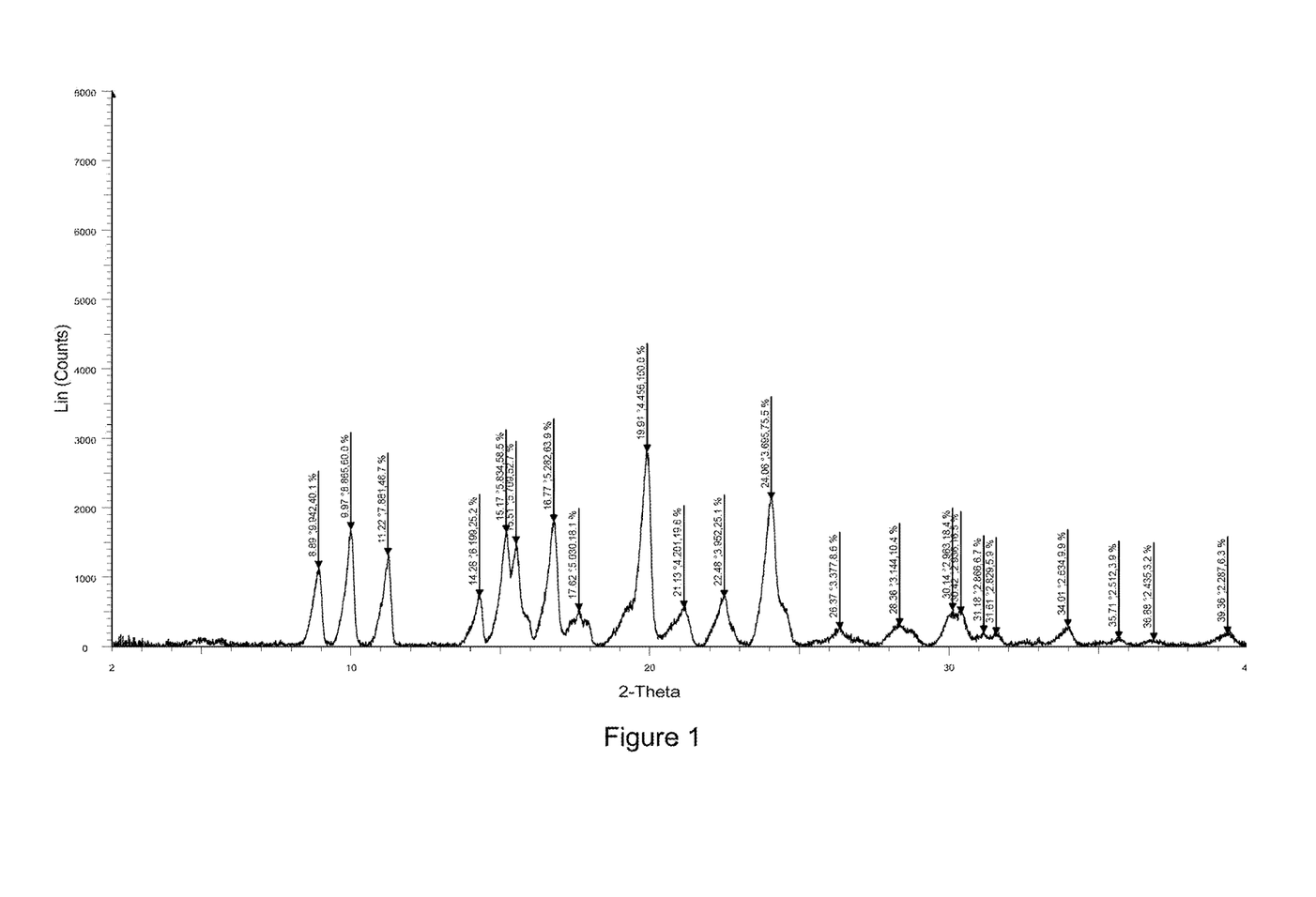
FIG. 1 shows the X-ray powder diffraction spectrum of crystal form I of the compound of formula (I).

The present invention provides a new crystal form of (S)-4-(3-(4-(2,3-dihydroxypropoxy)phenyl)-4,4-methyl-5- carbonyl-2-thioimidazolin-1-yl)-2-(trifluoromethyl)benzonitrile (as shown in formula (I)):

A series of crystal products of the compound of formula (I) have been obtained under various crystallization conditions, and X-ray diffraction and differential scanning calorimetry (DSC) measurements have been conducted on the obtained crystal products. It was found that a stable crystal form, which is referred to as crystal form I, can be obtained under normal crystallization conditions. The DSC spectrum of crystal form I of the present application shows a melting endothermic peak at about 157° C. The X-ray powder diffraction spectrum, which is obtained by using Cu-Ka radiation and represented by 2θ angle and interplanar distance (d value), is shown in FIG. 1, in which there are characteristic peaks at 8.89 (9.94), 9.97 (8.87), 11.22 (7.88), 14.28 (6.20), 15.17 (5.83), 15.51 (5.71), 16.77 (5.28), 19.91 (4.46), 21.13 (4.20), 22.48 (3.95), 24.06 (3.70), and 26.37 (3.38).

The present invention also provides a method for preparing crystal form I of (S)-4-(3-(4-(2,3-dihydroxypropoxy)phenyl)-4,4-methyl-5-carbonyl-2-thioimidazolin-1-yl)-2-(trifluoromethyl)benzonitrile, comprising the following steps of:

1) adding any crystal form or amorphous form of the compound of formula (I) into an appropriate amount of organic solvent, heating the solution until it is clear, and then cooling it to precipitate a crystal, wherein the solvent is selected from any one of esters, ketones, nitriles, and ethers, or a mixed solvent thereof; preferably, the solvent has 5 or less carbon atoms; and 2) filtering the crystal, then washing and drying it.

In a preferred embodiment, the solvent in step 1) is a single solvent selected from ethyl acetate, acetone, isopropyl acetate, tetrahydrofuran, and acetonitrile, and is acetone/isopropyl ether, ethyl acetate/n-hexane, ethyl acetate/isopropyl ether, or ethyl acetate/methyl tert-butyl ether; preferably ethyl acetate/isopropyl ether. The ratio of the two is not particularly limited, preferably between 1:10 and 10:1, and the volume ratio is 1:1 in an embodiment of the present invention.

The recrystallization method is not particularly limited, and can be carried out by a conventional recrystallization process. For example, the material, i.e., the compound of formula (I), can be dissolved in an organic solvent under heating, then the solution is cooled slowly to precipitate a crystal. After the completion of crystallization, the desired crystal can be obtained via filtering and drying. In particular, the crystal obtained by filtration is usually dried in a vacuum under reduced pressure at a heating condition of about 30 to 100° C., preferably 40 to 60° C., to remove the recrystallization solvent.

The resulting crystal form of the compound of formula (I) is determined by differential scanning calorimetry (DSC) and X-ray diffraction spectrum. Meanwhile, the residual solvent in the obtained crystal is also determined.

Crystal form I of the compound of formula (I) prepared according to the method of the present invention does not contain or contains only a relatively low content of residual solvent, which meets the requirement of the National Pharmacopoeia concerning the limitation of the residual solvent of drug products. Therefore, the crystal of the present invention is suitable for use as a pharmaceutical active ingredient.

The experimental results show that crystal form I of the compound of formula (I) prepared according to present invention is stable under conditions of lighting, high temperature and high humidity. Crystal form I is also stable under conditions of grinding, pressure and heating, which meets the production, transportation and storage requirements of drug products. The preparation process thereof is stable, repeatable and controllable, which is suitable for industrial production.

In another aspect, the present invention provides a pharmaceutical composition comprising crystal form I of the compound of formula (I), wherein the pharmaceutical composition comprises a crystal form of the compound of formula (I) and a pharmaceutically acceptable carrier.

In another aspect, the present invention relates to a use of crystal form I of the compound of formula (I) of the present invention or the pharmaceutical composition of the present invention in the preparation of a medicament for the treatment of a disease related to androgen receptor, wherein the disease is preferably prostate cancer.

DETAILED DESCRIPTION OF THE INVENTION

The present invention is illustrated by the following examples in detail. The examples of the present invention are merely intended to describe the technical solution of the present invention, and should not be considered as limiting the scope of the present invention.

Test instruments used in the experiments
1. DSC spectrum
Instrument type: Mettler Toledo DSC 1 Staree System
Purging gas: Nitrogen
Heating rate: 10.0° C./min
Temperature range: 40-250° C.
2. X-ray diffraction spectrum
Instrument type: Bruker D8 Focus X-ray powder diffractometer
Ray: monochromatic Cu-Kα ray (λ=1.5406)
Scanning mode: θ/2θ, Scanning range: 2-40°
Voltage: 40 KV, Electric current: 40 mA

Example 1

Figure 2:
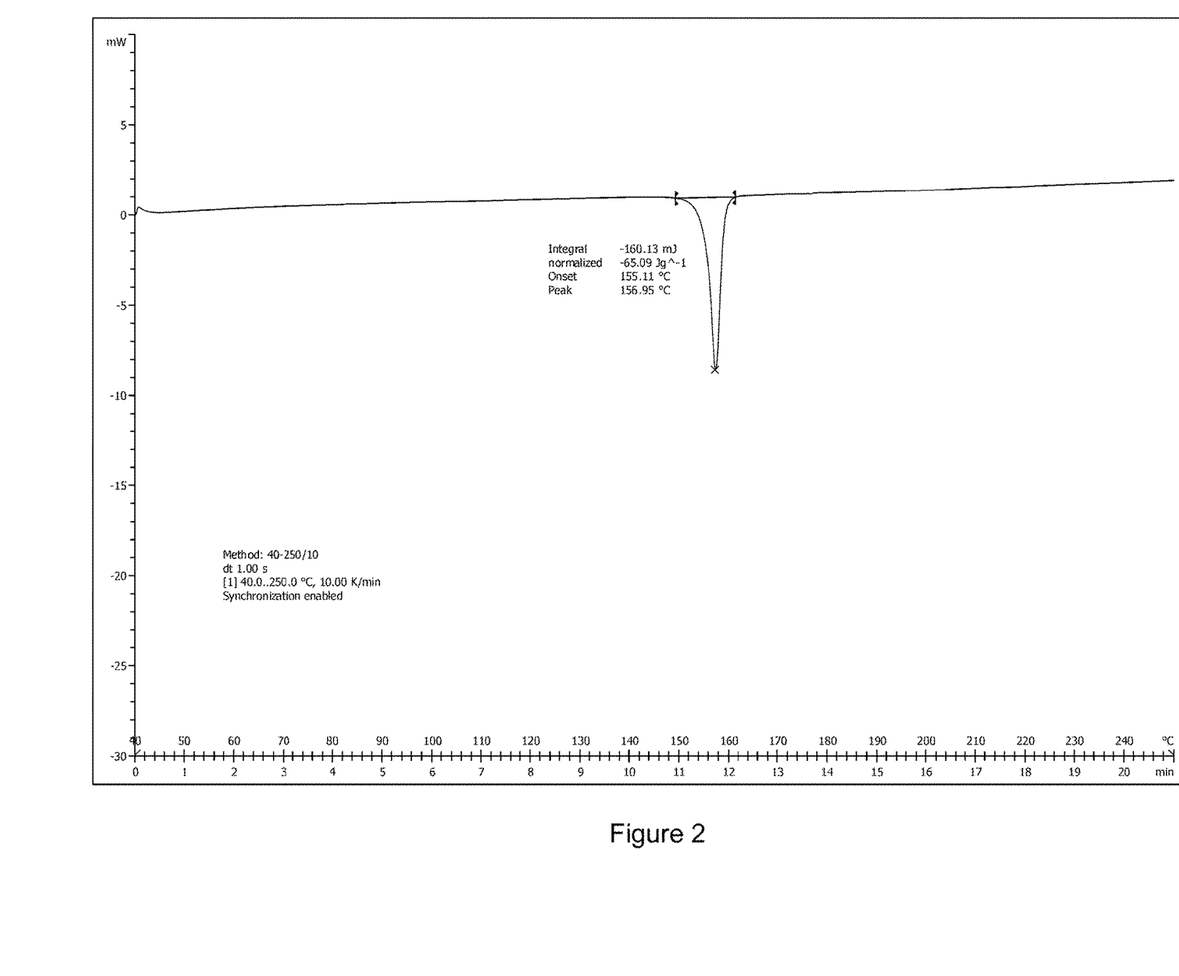
FIG. 2 shows the DSC spectrum of crystal form I of the compound of formula (I).
Figure 3:
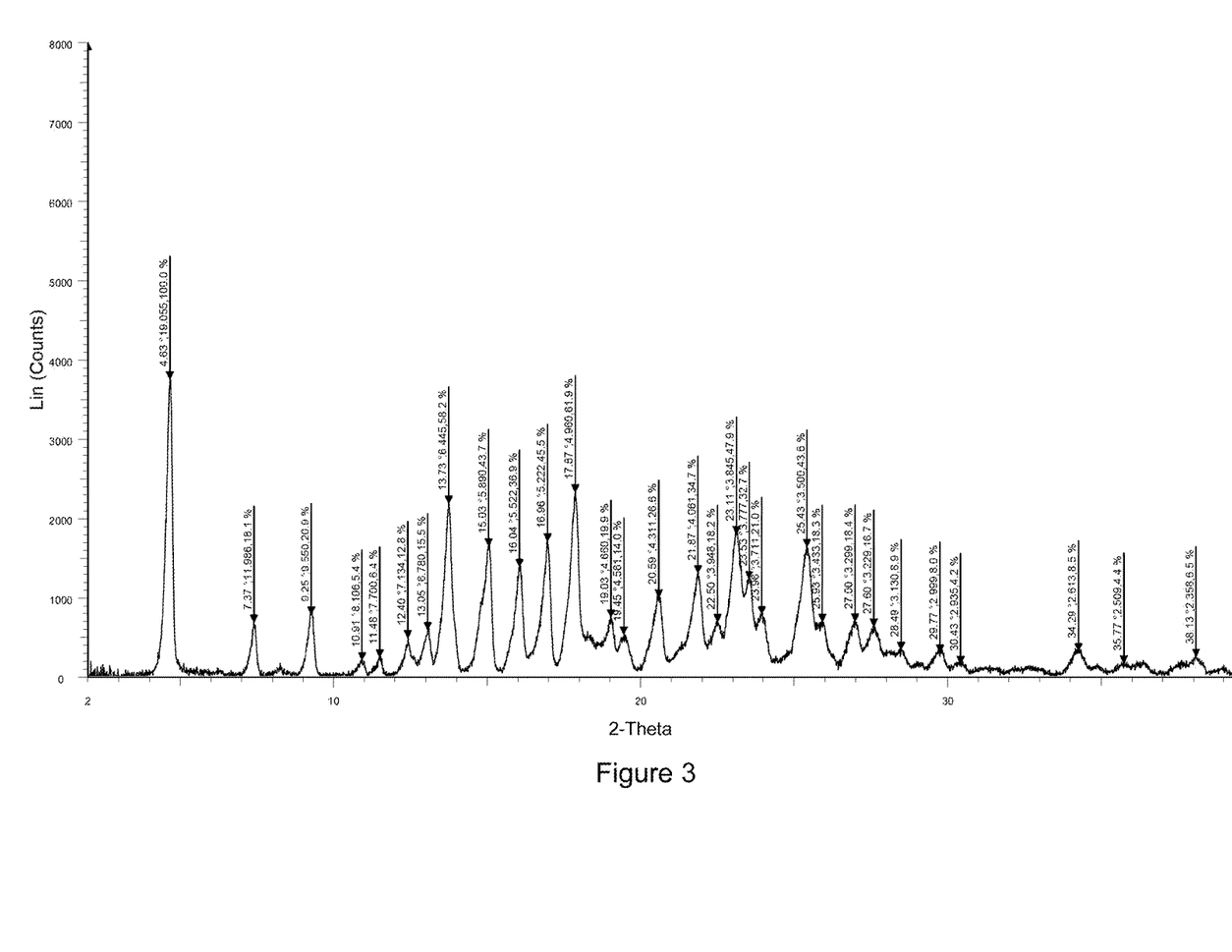
FIG. 3 shows the X-ray powder diffraction spectrum of crystal form II of the compound of formula (I).
Figure 4:
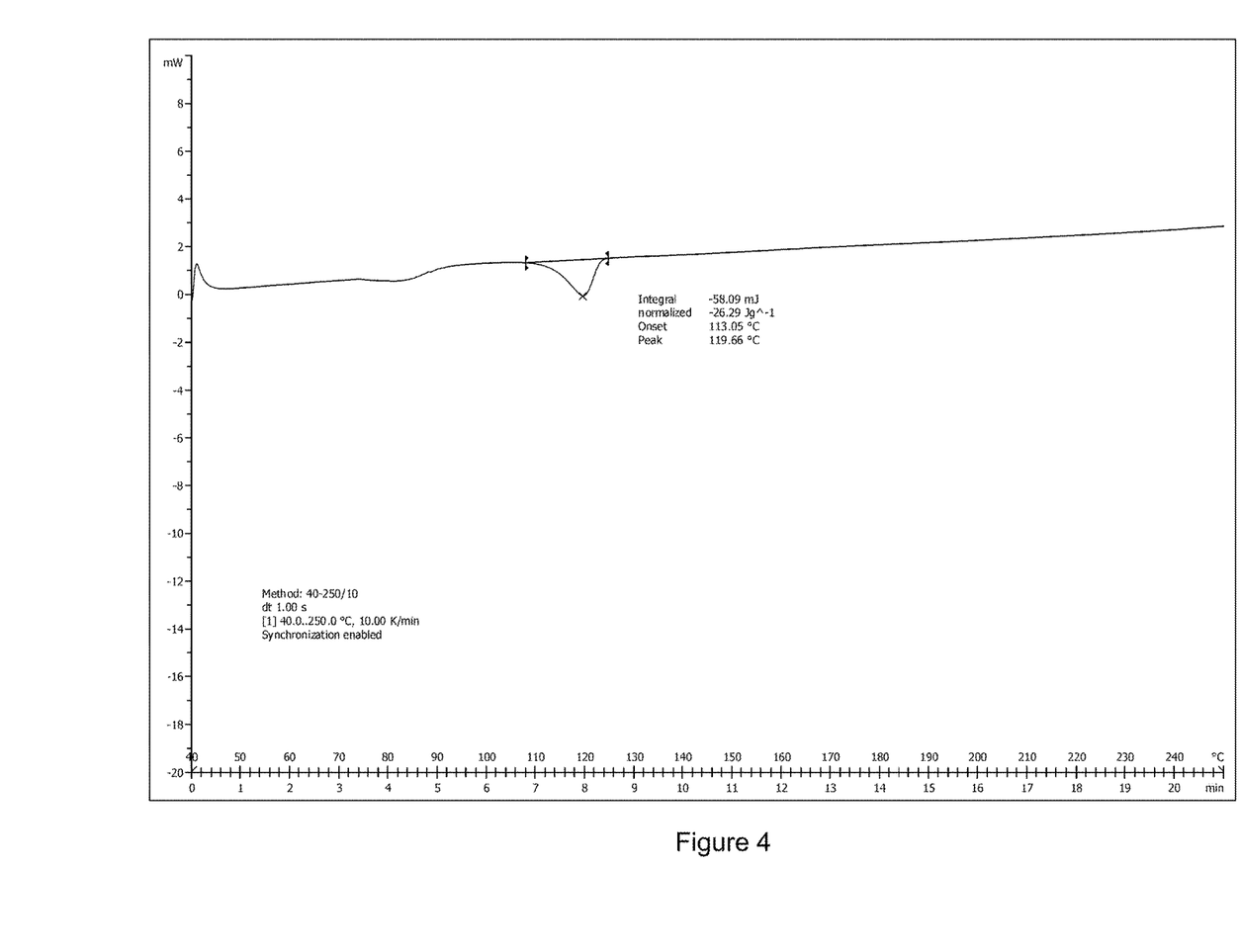
FIG. 4 shows the DSC spectrum of crystal form II of the compound of formula (I).
Figure 5:
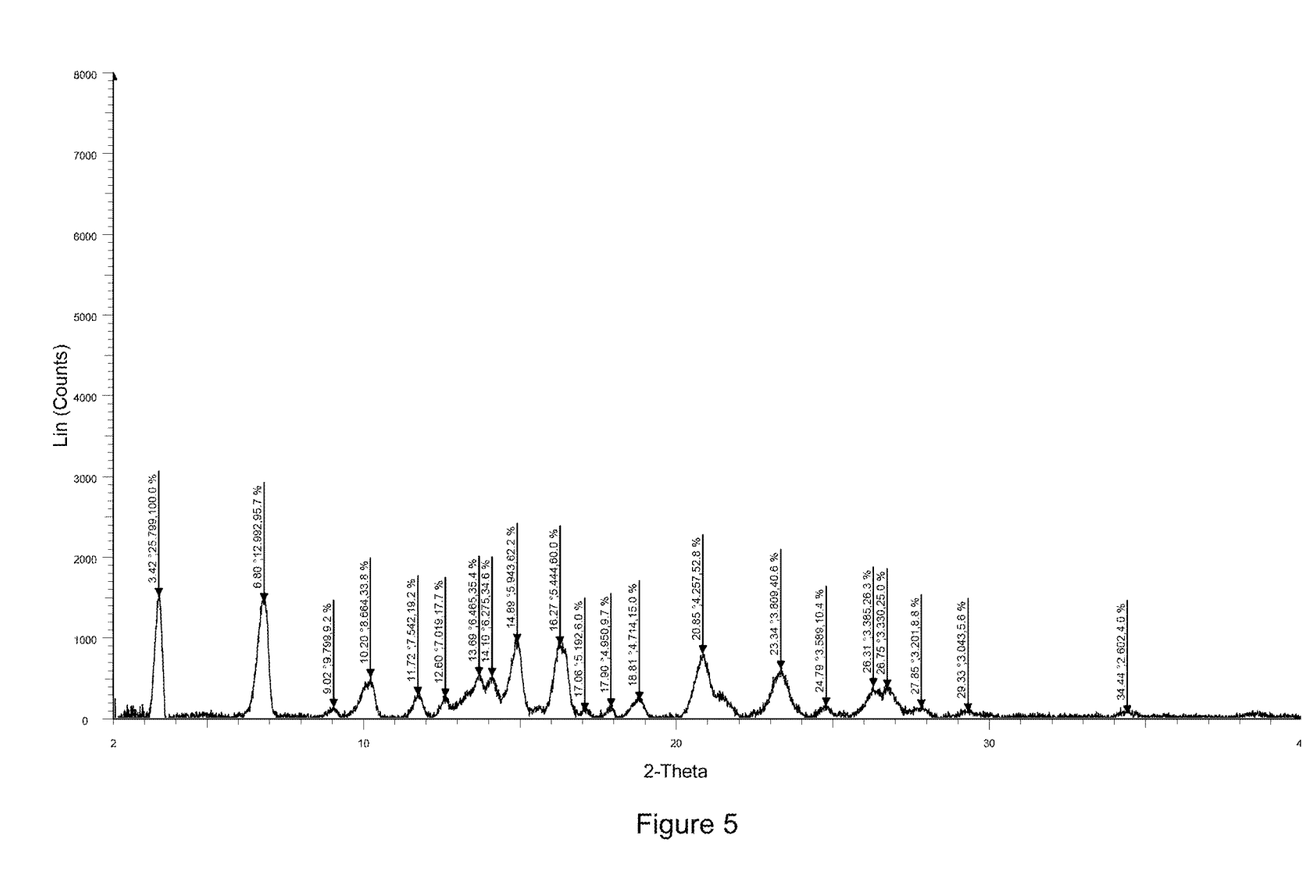
FIG. 5 shows the X-ray powder diffraction spectrum of crystal form III of the compound of formula (I).
Figure 6:
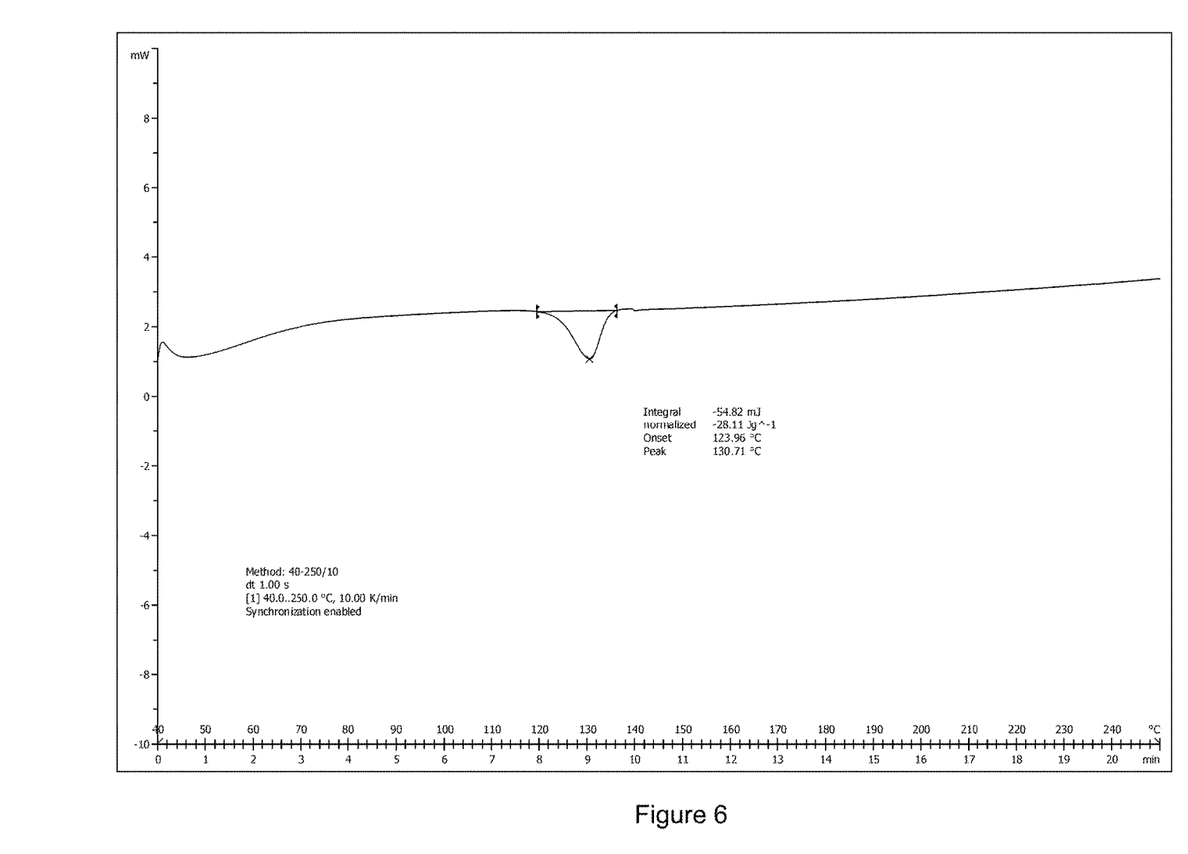
FIG. 6 shows the DSC spectrum of crystal form III of the compound of formula (I).

The compound of formula (I) (1.0 g, 2.09 mmol) (prepared according to the method provided in International Patent Application Publication WO2014036897A1) was added to a 25 ml one-necked flask, followed by addition of 4.0 mL of ethyl acetate. The mixture was heated to reflux until the solution was clear. The solution was continuously refluxed for 10 minutes, then cooled to precipitate a crystal under stirring. The mixture was filtered and dried to obtain a solid (560 mg, yield: 56.0%). The X-ray powder diffraction spectrum of the crystal sample is shown in FIG. 1, in which there are characteristic peaks at about 8.89 (9.94), 9.97 (8.87), 11.22 (7.88), 14.28 (6.20), 15.17 (5.83), 15.51 (5.71), 16.77 (5.28), 19.91 (4.46), 21.13 (4.20), 22.48 (3.95), 24.06 (3.70), and 26.37 (3.38). The DSC spectrum is shown in FIG. 2, having a sharp melting endothermic peak at 157° C. The crystal form was defined as crystal form I.

Example 2

The compound of formula (I) (1.0 g, 2.09 mmol) (prepared according to Example 1) was added to a 25 mL one-necked flask, followed by addition of 4.0 mL of acetone. The mixture was heated to reflux until the solution was clear. The solution was continuously refluxed for 10 minutes, then cooled to precipitate a crystal under stirring. The mixture was filtered and dried to obtain a solid (438 mg, yield: 43.8%). The product was identified as crystal form I after studying and comparing the X-ray diffraction and DSC spectra.

Example 3

The compound of formula (I) (1.0 g, 2.09 mmol) (prepared according to Example 1) was added to a 25 mL one-necked flask, followed by addition of 4.0 mL of ethyl acetate. The mixture was heated to reflux until the solution was clear, then 4.0 mL of n-hexane was added dropwise. The mixture was continuously refluxed for 10 minutes, then cooled to precipitate a crystal under stirring. The mixture was filtered and dried to obtain a solid (711 mg, yield: 71.1%). The product was identified as crystal form I after studying and comparing the X-ray diffraction and DSC spectra.

Example 4

The compound of formula (I) (1.0 g, 2.09 mmol) (prepared according to Example 1) was added to a 25 mL one-necked flask, followed by addition of 5.0 mL of ethyl acetate. The mixture was heated to reflux until the solution was clear, then 5.0 mL of isopropyl ether was added dropwise. The mixture was continuously refluxed for 10 minutes, then cooled to precipitate a crystal under stirring. The mixture was filtered and dried to obtain a solid (678 mg, yield: 67.8%). The product was identified as crystal form I after studying and comparing the X-ray diffraction and DSC spectra.

Example 5

The compound of formula (I) (1.0 g, 2.09 mmol) (prepared according to Example 1) was added to a 25 mL one-necked flask, followed by addition of 5.0 mL of ethyl acetate. The mixture was heated to reflux until the solution was clear, then 5.0 mL of methyl tert-butyl ether was added dropwise. The mixture was continuously refluxed for 10 minutes, then cooled to precipitate a crystal under stirring. The mixture was filtered and dried to obtain a solid (682 mg, yield: 68.2%). The product was identified as crystal form I after studying and comparing the X-ray diffraction and DSC spectra.

Example 6

The compound of formula (I) (1.0 g, 2.09 mmol) (prepared according to Example 1) was added to a 25 mL one-necked flask, followed by addition of 6.0 mL of isopropyl acetate. The mixture was heated to reflux until the solution was clear. The solution was continuously refluxed for 10 minutes, then cooled to precipitate a crystal under stirring. The mixture was filtered and dried to obtain a solid (612 mg, yield: 61.2%). The product was identified as crystal form I after studying and comparing the X-ray diffraction and DSC spectra.

Example 7

The compound of formula (I) (1.0 g, 2.09 mmol) (prepared according to Example 1) was added to a 25 mL one-necked flask, followed by addition of 5.0 mL of acetone. The mixture was heated to reflux until the solution was clear, then 5.0 mL of water was added dropwise. The mixture was continuously refluxed for 10 minutes, then cooled to precipitate a crystal under stirring. The mixture was filtered and dried to obtain a solid (476 mg, yield: 47.6%). The product was identified as crystal form I after studying and comparing the X-ray diffraction and DSC spectra.

Example 8

The compound of formula (I) (1.0 g, 2.09 mmol) (prepared according to Example 1) was added to a 25 mL one-necked flask, followed by addition of 5.0 mL of acetone. The mixture was heated to reflux until the solution was clear, then 5 mL of isopropyl ether was added dropwise. The mixture was continuously refluxed for 10 minutes, then cooled to precipitate a crystal under stirring. The mixture was filtered and dried to obtain a solid (521 mg, yield: 52.1%). The product was identified as crystal form I after studying and comparing the X-ray diffraction and DSC spectra.

Example 9

The compound of formula (I) (1.0 g, 2.09 mmol) (prepared according to Example 1) was added to a 25 mL one-necked flask, followed by addition of 2.0 mL of tetrahydrofuran. The mixture was heated to reflux until the solution was clear. The solution was continuously refluxed for 10 minutes, then cooled to precipitate a crystal under stirring. The mixture was filtered and dried to obtain a solid (327 mg, yield: 32.7%). The product was identified as crystal form I after studying and comparing the X-ray diffraction and DSC spectra.

Example 10

The compound of formula (I) (1.0 g, 2.09 mmol) (prepared according to Example 1) was added to a 25 mL one-necked flask, followed by addition of 2.0 mL of acetonitrile. The mixture was heated to reflux until the solution was clear. The solution was continuously refluxed for 10 minutes, then cooled to precipitate a crystal under stirring. The mixture was filtered and dried to obtain a solid (242 mg, yield: 24.2%). The product was identified as crystal form I after studying and comparing the X-ray diffraction and DSC spectra.

Example 11

The entire procedure of Example 44 of International Patent Application Publication WO2014036897A1 was repeated. (R)-4-(3-(4-((2,2-Dimethyl-1,3-dioxolan-4-yl) methoxy)phenyl)-4,4-dimethyl-5-oxo-2-thioxoimidazolidin-1-yl)-2-(trifluoromethyl)benzonitrile (2.2 g, 4.20 mmol) was dissolved in 100 mL of acetic acid, followed by addition of 50 mL of water. The reaction solution was warmed up to 70° C., and stirred for 1 hour. Then, the reaction solution was concentrated under reduced pressure to remove acetic acid, added with 100 mL of water and 100 mL of ethyl acetate, and left to stand and separate. The organic phase was washed with saturated sodium bicarbonate solution, dried over anhydrous sodium sulfate, and filtered. The filtrate was concentrated under reduced pressure, and the residue was purified by silica gel chromatography to obtain a crystal of compound I (1.1 g, 55.0%). The crystal sample was identified not as crystal form I after studying and comparing the X-ray diffraction and DSC spectra, then it was defined as crystal form III herein.

Example 12

The compound of formula (I) (1.0 g, 2.09 mmol) (prepared according to Example 1) was added to a 25 mL one-necked flask, followed by addition of 5.0 mL of methanol. The mixture was heated to reflux until the solution was clear. The solution was continuously refluxed for 10 minutes, then cooled to precipitate a crystal under stirring. The mixture was filtered and dried to obtain a solid (516 mg, yield: 51.6%). This crystal has characteristic peaks at about 4.63 (19.06), 7.37 (11.99), 9.25 (9.55), 10.91 (8.11), 11.48 (7.70), 12.40 (7.13), 13.05 (6.78), 13.73 (6.45), 15.03 (5.89), 16.04 (5.52), 16.96 (5.22), 17.87 (4.96), 19.03 (4.66), 19.45 (4.56), 20.59 (4.31), 21.87 (4.06), 22.50 (3.95), 23.11 (3.85), 23.53 (3.78), 23.96 (3.71), 25.43 (3.50), 27.00 (3.30), 27.60 (3.23), and 29.77 (3.00). The DSC spectrum is shown in FIG. 2, having a sharp melting endothermic peak at 119° C. The crystal form was defined as crystal form II.

Example 13

The compound of formula (I) (0.5 g, 1.04 mmol) (prepared according to Example 1) and the compound of formula (I) (0.5 g, 1.04 mmol) (prepared according to Example 11) were added to a 25 mL one-necked flask, followed by addition of 4.0 mL of ethyl acetate-isopropyl ether (v:v=1: 1). The mixture was pulped at room temperature, then filtered and dried to obtain a solid (872 mg, yield: 87.2%). The product was identified as crystal form I after studying and comparing the X-ray diffraction and DSC spectra. It can be seen that crystal form III can be transformed into crystal form I at room temperature, confirming that crystal form I is more stable.

Example 14

The compound of formula (I) (0.5 g, 1.04 mmol) (prepared according to Example 1) and the compound of formula (I) (0.5 g, 1.04 mmol) (prepared according to Example 12) were added to a 25 mL one-necked flask, followed by addition of 4.0 mL of ethyl acetate-isopropyl ether (v:v=1: 1). The mixture was pulped at room temperature, then filtered and dried to obtain a solid (850 mg, yield: 85.0%). The product was identified as crystal form I after studying and comparing the X-ray diffraction and DSC spectra. It can be seen that crystal form II can be transformed into crystal form I at room temperature, confirming that crystal form I is more stable.

Example 15

The sample of crystal form I prepared in Example 1 was spread flat in the air to test its stability under conditions of lighting (4500 Lux), heating (40° C., 60° C.), and high humidity (RH 75%, RH 90%). Samplings were carried out on Day 5 and Day 10. The purity as detected by HPLC is shown in Table 1.

TABLE 1

Stability comparison of the sample of crystal form I of the compound of formula (I)

| Batch number | Time (day) | Lighting | 40° C. | 60° C. | RH 75% | RH 90% |
|---|---|---|---|---|---|---|
| Crystal form I | 0 | 99.93% | 99.93% | 99.93% | 99.93% | 99.93% |
|  | 5 | 99.91% | 99.91% | 99.92% | 99.89% | 99.92% |
|  | 10 | 99.91% | 99.91% | 99.90% | 99.91% | 99.92% |

The results of the stability study showed that the sample of crystal form I of the compound of formula (I) had good stability when it was spread flat in the air under conditions of lighting, high temperature and high humidity.

Example 16

Crystal form I of the compound of formula (I) prepared according to the method of Example 1 was ground, heated and pressed. The results showed that the crystal form is stable. The detailed experimental data are shown in Table 2 below.

TABLE 2

Special stability study of crystal form I of the compound of formula (I)

| Batch number | Treatment Process | Experimental procedure | Crystal form | DSC peak |
|---|---|---|---|---|
| S011204130515G | Grinding treatment for 10 minutes | 1 g of the sample of crystal form I of the compound of formula (I) was ground for 10 minutes in a mortar under nitrogen atmosphere. | Crystal form I | 158.26° C. |

TABLE 2-continued

Special stability study of crystal form I of the compound of formula (I)

| Batch number | Treatment Process | Experimental procedure | Crystal form | DSC peak |
| --- | --- | --- | --- | --- |
| S011204130515H | Heating treatment for 3 hours at 80° C. | 1 g of the sample of crystal form I of the compound of formula (I) was spread flat and heated at 80° C. for 3 hours. | Crystal form I | 158.17° C. |
| S011204130515P | Pressing treatment | The sample of crystal form I of the compound of formula (I) was pressed to a slice. | Crystal form I | 158.33° C. |

Example 17

The sample of crystal form I of the compound of formula (I) prepared according to Example 1 was spread flat in the air to test its stability during long-term storage at room temperature (25° C., RH 60%). The detailed experimental data are shown in Table 3 below.

TABLE 3

Stability test of the sample of crystal form I of the compound of formula (I) under reserving condition at room temperature

| Batch number | Time (month) | Crystal form | Purity (%) |
| --- | --- | --- | --- |
| S011204130515 | 0 | Crystal form I | 99.93 |
| | 6 | Crystal form I | 99.93 |
| | 12 | ND | 99.93 |
| | 24 | ND | 99.93 |
| | 36 | Crystal form I | 99.94 |

The sample was placed under conditions of 25° C., RH 60% for a long period of time, and regular sampling was carried out to determine the purity. The results showed that the crystal form of the sample is stable, and there is no significant change in purity, indicating that the sample is stable after placing under such conditions for 36 months.

What is claimed is:

1. A crystal form I of a compound of formula (I):

(I)

wherein the crystal form I has a characteristic X-ray powder diffraction spectrum comprising peaks at diffraction angles (2θ) of about 9.97, 15.17, 16.77, 19.91, and 24.06.

2. A crystal form I of a compound of formula (I):

(I)

wherein the crystal form I has a characteristic X-ray powder diffraction spectrum as shown in FIG. 1.

3. The crystal form I of the compound of formula (I) according to claim 1, further comprising peaks at diffraction angles (2θ) of about 9.97, 15.17, 16.77, 19.91, and 24.06.

4. A pharmaceutical composition, comprising the crystal form I of the compound of formula (I) according to claim 1, and a pharmaceutically acceptable carrier.

5. A pharmaceutical composition, comprising the crystal form I of the compound of formula (I) according to claim 2, and a pharmaceutically acceptable carrier.

6. A method of preparing the crystal form I of the compound of formula (I) according to claim 1, comprising:
(a) adding any crystal form or amorphous form of the compound of formula (I) into an organic solvent to obtain a solution, heating the solution until it is clear, and then cooling the solution to precipitate a crystal, wherein the organic solvent is selected from the group consisting of esters, ketones, nitriles, and ethers, each of which having 5 or less carbon atoms, or a mixture thereof; and
(b) filtering the crystal, then washing and drying the filtered crystal form I.

7. The method according to claim 6, wherein the solvent in (a) is a single solvent selected from the group consisting of ethyl acetate, acetone, isopropyl acetate, tetrahydrofuran, and acetonitrile, or the solvent is a mixed solvent comprising a mixture of acetone and isopropyl ether; a mixture of ethyl acetate and n-hexane; a mixture of ethyl acetate and isopropyl ether; or a mixture of ethyl acetate and methyl tert-butyl ether.

8. The method according to claim 7, wherein a volume ratio of the two solvents in the mixed solvent is 1:10 to 10:1.

9. The method according to claim 7, wherein the solvent is a mixed solvent comprising a mixture of ethyl acetate and isopropyl ether.

10. A method of treating an androgen receptor-related disease in a subject in need thereof, the method comprising administering to the subject the pharmaceutical composition of claim 4.

11. The method according to claim 10, wherein the androgen receptor-related disease is prostate cancer.

12. A method of treating an androgen receptor-related disease in a subject in need thereof, the method comprising administering to the subject the pharmaceutical composition of claim 5.

13. The method according to claim 12, wherein the androgen receptor-related disease is prostate cancer.

14. A method of inhibiting androgen receptor in a subject in need thereof, the method comprising administering to the subject the pharmaceutical composition of claim 4.

15. A method of inhibiting androgen receptor in a subject in need thereof, the method comprising administering to the subject the pharmaceutical composition of claim 5.

16. The method according to claim 7, wherein a volume ratio of the two solvents in the mixed solvent is 1:1.

* * * * *